United States Patent [19]
Ahmed et al.

[11] Patent Number: 5,825,293
[45] Date of Patent: Oct. 20, 1998

[54] APPARATUS AND METHOD FOR MONITORING BREATHING MAGNETICALLY

[76] Inventors: Adel A. Ahmed, 160 Ridgeview Cir., Princeton, N.J. 08540; Hassan Hakki, Hünibach-Strasse 40, 3652 Hilterfingen, Switzerland

[21] Appl. No.: 717,489

[22] Filed: Sep. 20, 1996

[51] Int. Cl.$^6$ .................................................. G08B 21/00
[52] U.S. Cl. ............................ 340/573; 128/716; 128/721
[58] Field of Search ........................... 340/573; 128/721, 128/716

[56] References Cited

U.S. PATENT DOCUMENTS

| | | | |
|---|---|---|---|
| 3,911,899 | 10/1975 | Hattes | 128/653.1 |
| 4,197,856 | 4/1980 | Northrop | 128/661.07 |
| 4,296,757 | 10/1981 | Taylor | 128/721 |
| 4,696,307 | 9/1987 | Montgieux | 128/721 |
| 5,038,785 | 8/1991 | Blakely et al. | 128/653 A |
| 5,309,922 | 5/1994 | Schechter et al. | 128/721 |
| 5,311,875 | 5/1994 | Stasz | 128/724 |
| 5,360,008 | 11/1994 | Campbell, Jr. | 128/671 |
| 5,454,376 | 10/1995 | Stephens et al. | 128/721 |

OTHER PUBLICATIONS

"Sudden Infant Death Syndrome Among American Indians: United States 1983–1987", G. Pezzino and S. Iyasu, Journal of Sudden Infant Death Syndrome and Infant Mortality, vol. 1, No. 1, 1996; pp. 3–6.

"SIDS Is Not Always Truly Sudden", R. Meny et al., Journal of Sudden Death Syndrome and Infant Mortality, vol. 1, No. 1, 1996; pp. 50–52.

"Home Monitoring in Infants at Risk for SIDS", Heather Bryan, pp. 459–464. *Sudden Infant Death Syndrome, Risk Factors & Basic Mechanisms*, PMA Publishing Corp., 1988.

"Control of Breathing in Fetal Life and Onset and Control of Breathing in the Neonate", Chapter 75, H. Rigatto; pp. 790–801, *Fetal and Neontal Physiology*, Editors Polin and Fox, W. B. Saunders Company, 1992.

"Measurements of Respiratory Mechanics", Chapter 77, J. P. Mortola; pp. 812–821. *Fetal and Neonatal Physiology*, Editors Polin and Fox, W.B. Saunders Company, 1992.

3 pages downloaded from Internet : John Lighton (Sablesys@aol.com; lighton@nevada.edu; Oct. 21, 1995; esp. pp. 2 and 3; 702-895-3967); Society for Amateur Scientists, 4951 D Clairemont Square Suite 179, San Diego, CA 92117 Phone/Fax: (619) 239–8807, Outside 619 area code (800)–873–8767; Internet: info@sas.org.

2 pages downloaded from Internet: FMlms@aol.com: Nov. 3, 1995; esp. article on page 1 and article bridging pp. 1 and 2; Society for Amateur Scientists, 4951 D Clairemont Square Suite 179, San Diego, CA 92117 Phone/Fax: (619) 239–8807, Outside 619 area code: (800)–873–8767; Internet: info@sas.org.

1 page downloaded from Internet: Herb Helbig<helbigh.1234@worldnet.att.net>; Sep. 16, 1996, esp. paragraphs 1,2,5, and 6; Society for Amateur Scientists, 4951 D Clairemont Square Suite 179, San Diego, CA 92117 Phone/Fax: (619) 239–8807, Outside 619 area code: (800)–873–8767: Internet: info@sas.org.

*Primary Examiner*—Glen Swann

[57] ABSTRACT

Apparatus for monitoring breathing and for indicating a rate of breathing outside of a predetermined rate limit includes a sensing element adapted to be worn by a wearer so that the sensing element partakes of body motion due to breathing of the wearer and a detector, remote from the sensing element. The detector is responsive to motion of the sensing element for providing an alarm signal when the motion is outside of the predetermined rate limit. The sensing element contains no internal moving parts or circuitry, contains no battery or other source of electrical power whatsoever, requires no electrical contact with the wearer or with any other object, and requires no constraining or confining clothing, webbing, or the like. The sensing element includes a permanent magnet and the detector includes a magnetic detector for monitoring a magnetic field caused by the magnet and for providing the alarm signal when a measured rate of variation of the magnetic field is detected to be outside of the predetermined rate limit. Thus, the alarm signal indicates the rate of breathing to be outside of the predetermined rate limit.

41 Claims, 10 Drawing Sheets

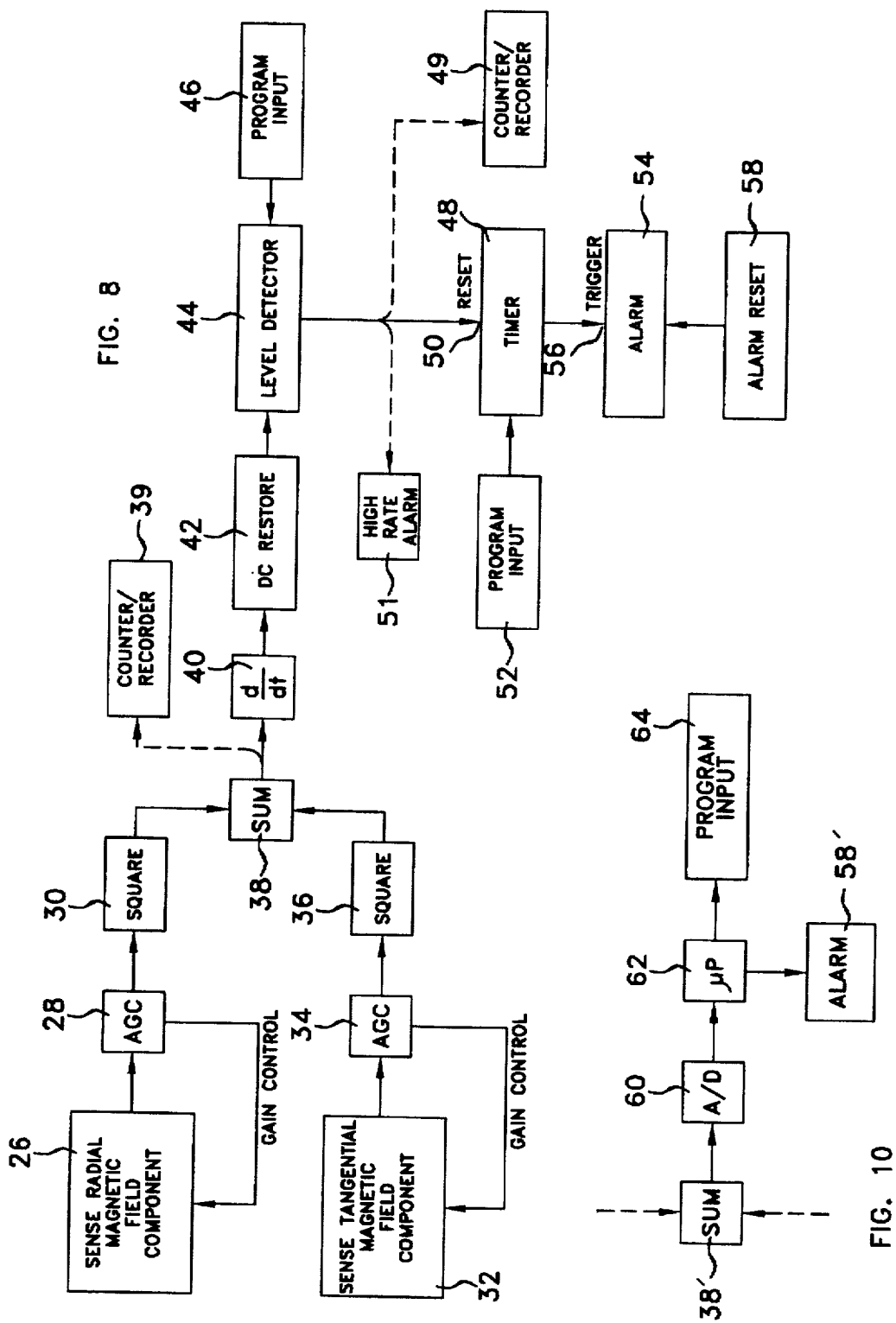

APPARATUS AND METHOD FOR MONITORING BREATHING MAGNETICALLY

The present invention relates to breathing monitors and, more specifically, to breathing monitors for monitoring a cessation or interruption of normal breathing, such as may occur in sleep apnea and, for example, sudden infant death syndrome (SIDS).

Sudden infant death syndrome is a not uncommon occurrence: for some reason, generally not fully explicable, a child stops breathing. In the ensuing silence, typically no alarm is raised and the cessation of breathing is not recognized by a parent or attendant, often until it is too late and life has ceased. Furthermore, suffocation can also occur from a variety of other causes, such as entanglement in bed clothing, blankets, plastic bags and the like, leading to a silent process of suffocation.

It is also recognized that apnea in infants can be caused by gastroesophageal reflex, pharyngeal incoordination, convulsion, heart disease, infection, DVS abnormality, accidental smothering and breath-holding spells. In each case, the condition is not immediately apparent to others and the cessation of breathing may go unrecognized for a time.

Breathing monitors are presently utilized in hospitals. Generally, such breathing monitors tend to be expensive and somewhat elaborate.

Examples of breathing monitoring apparatus and methods may be found in the following, for example.

U.S. Pat. No. 5,454,376, issued Oct. 13, 1995 in the name of Stephens et al. discloses a breathing monitor article of apparel, utilizing an electronically operated monitor for generating an alarm signal;

U.S. Pat. No. 5,360,008, issued Nov. 1, 1994 in the name Campbell, Jr. discloses an apnea detector utilizing a discovery that the magnetic permeability of a person's body varies with the respiratory and cardiac cycles. Signals are utilized which are modulated due to the varying permeability of the body caused by respiratory and cardiac cycles;

U.S. Pat. No. 5,311,875, issued May 17, 1994, in the name of Stasz discloses a flexible compliant film transducer exhibiting piezoelectric and pyroelectric properties for sensing breathing;

U.S. Pat. No. 5,309,922, issued May 10, 1994, in the name of Schechter et al. discloses a respiratory sound analyzer for use in high noise environments;

U.S. Pat. No. 5,038,785, issued Aug. 13, 1991, in the name of Blakeley et al. discloses a cardiac and respiratory monitor with magnetic gradient noise elimination. A magnetic resonance imaging apparatus generates a uniform magnetic field, causes gradient fields transversely thereacross, excites resonance in nuclei within the image region, receives radio frequency signals from resonating nuclei and reconstructs images representative thereof;

U.S. Pat. No. 4,696,307, issued Sep. 29, 1987, in the name of Montgieux discloses a device for detecting breathing rhythm and being housed in a small box to be laid directly on the body of a child; and U.S. Pat. No. issued 4,296,757, issued Oct. 27, 1981, in the name of Taylor discloses a respiratory monitor for detecting expansion of the chest.

It will be noted that, typically, prior art monitors require some form of active electrical equipment to be adjacent the subject's body.

Prior art monitors also generally tend to be complex and therefore expensive and more complicated to adjust and operate. Complexity in the apparatus also tends to lead to a higher rate of failure, typically resulting in a higher number of false alarms. Given the potentially serious nature of an alarm, false alarms are productive of unnecessary anxiety and disturbance and are most undesirable in an apnea monitor. See, for example, Sudden Infant Death Syndrome, 33, "Risk Factors and Basic Mechanisms", Editors: Ronald M. Harper, Howard J. Hoffman; 1988 PMA Publishing Corp. ISBN 0-89335-248-9, "Home Monitoring in Infants at Risk for SIDS", Heather Bryan, pp. 459–464 at page 462, stating, in reference to tests conducted over an period of time, that "(F)alse alarms occurred in 65% of the infants on home monitors and were frequent in one third. While alarms due to electrical faults were more common in monitors with chest leads and were more easily identified and corrected, all false alarms caused anxiety and were a nuisance to the family. False alarms occurred more frequently in older, active infants and in 20 infants were difficultly to correct. In these severe cases, the type of monitor was changed, which often, but not always, led to a reduction in the number of false alarms."

Most prior art monitors require some sort of maintenance, at least for battery replacement. Furthermore, when apparatus is integrally attached to bed clothing for an infant, removal and subsequent reattachment is generally required for changing clothing and laundering.

Furthermore, it is herein recognized that the attachment of active systems, utilizing batteries, electrodes, and electrical leads to an infant is undesirable for a number of reasons. Installation of leads is troublesome, sometimes irritating, and often prone to detachment and consequent false alarms.

Connection to equipment containing sources of electrical power is also undesirable from a safety aspect, even when isolating elements such as capacitors or high value resistors are utilized. It is known that the continuous application for a long period of time of relatively small electrical currents through internal organs may cause problems. Electrical components, even those of the highest quality, are liable to failure and a resulting application of even relatively "harmless" low voltages to an infant's body for possibly a prolonged period of time may have health consequences.

It is also not desirable to constrain an infant's body, such as by a jacket or belt, so as to enable a force sensor to measure chest or abdominal expansion and contraction as an indication of breathing. By its nature, such a measurement of force must result in a reaction force in the body, which will constrain to some extent the respiratory movements of the chest and abdomen which the infant is attempting to make so as to breath. Another possible reason to avoid any type of confining article of wear is that the application of continuous negative pressure around the chest tends to abolish apnea. See Fetan and Neonatal Physiology: Editors: Richard A. Polin, William W. Fox. 1992 W. B. Saunders Company. ISBN 0-7216-2963-6—ISBN 0-7216-3515X—ISBN 0-7216-3514-8. The Lung, Chapter 75, by Henrique Rigatto, pp. 790–801, at page 797. This gives rise to a possible inference that a positive pressure around the chest may increase the probability of apnea.

Normal breathing, particularly in an infant, is subject to a range of values with regard to its frequency, regularity, volumetric extent, and the relative amount of the movement involved of the chest and abdominal walls. It is therefore desirable to avoid utilizing a pressure transducing mechanical system, in which it may be problematic to depend on pressure variations relative to a fixed belt or article of clothing to provide a dependable indication of normal breathing.

Nevertheless, despite a wide range of variables, it is possible to fix an acceptable rate as being in the neighborhood of 9 breaths per minute and to define a period of apnea exceeding 20 seconds as warranting an alarm.

Published data is available for infant breathing characteristics. See, for example, Fetal and Neonatal Physiology: Editors: Richard A. Polin, William W. Fox. 1992 W. B. Saunders Company. ISBN 0-7216-2963-6—ISBN 0-7216-3515X—ISBN 0-7216-3514-8, The Lung, Chapter 77, Measurements of Respiratory Mechanics by Jacopo P. Mortola, pp. 813–821 and Chapter 75, by Henrique Rigatto, pp. 790–801. The data indicates that infant breathing is predominantly abdominally induced, with abdominal wall movement being in the range of 5 centimeters (cm) peak to peak and chest wall movement being in the range of 0.5 cm (see Rigatto, cited above, page 796, FIG. 75-10). A case is also shown with about 2 cm of abdomen motion, peak to peak. See Mortola, cited above, page 819, FIG. 77-5.

Apnea is also defined in Rigatto, cited above, as a pause in breathing lasting longer than 20 seconds and is stated to be more frequent during periods of Rapid Eye Movement (REM) sleep than in quiet sleep.

It is herein recognized that regular movement of at least one of (a) the chest wall and (b) the abdominal wall, with an amplitude exceeding a prescribed minimum, is a reliable indicator that breathing is occurring, whether of the REM type or otherwise.

In accordance with an exemplary embodiment of the invention, a small permanent magnet is affixed to an infant's body, preferably through the intermediary of an article of clothing. The location of the magnet is such that it is carried by the abdominal wall, or the chest wall, so that it moves in common therewith. That is, the magnet will primarily move to and fro with the same motion as the abdominal or chest wall. Its motion will thus be primarily alternatingly translational with possibly a small incidental alternating rotation. The permanent magnet is of small size and is completely passive, without need of any batteries, electrodes, or wires or other accessories.

No confining clothing, harness, or belting is required. It may be convenient to encase the magnet in a pocket, pouch, or purse of suitable fabric. Conveniently, the magnet pouch may have a surface of Velcro™ for convenient attachment to a corresponding portion of the child's clothing. The weight of the small magnet utilized is so small that it represents a negligibly small burden, even for a very small infant and it in no way constrains or restricts the natural movements associated with breathing or otherwise occurring. In accordance with an aspect of the invention, apparatus for monitoring breathing and for indicating a rate of breathing outside of a predetermined rate limit, includes a sensing element adapted to be worn by a wearer so that the sensing element partakes of body motion due to breathing of the wearer and a detector, remote from the sensing element, and being responsive to motion of the sensing element for providing an alarm signal when the motion is outside of the predetermined rate limit, wherein the sensing element contains no internal moving parts or circuitry, contains no battery or other source of electrical power whatsoever, requires no electrical contact with the wearer or with any other object, and requires no constraining or confining clothing, webbing, or the like. The sensing element comprises permanent magnet apparatus and the detector comprises magnetic detector apparatus for monitoring a magnetic field caused by the magnet and for providing the alarm signal when a measured rate of variation of the magnetic field is detected to be outside of the predetermined rate limit, whereby the alarm signal indicates the rate of breathing to be outside of the predetermined rate limit.

In accordance with another aspect of the invention, apparatus for monitoring breathing, includes a sensing element adapted to be worn by a wearer so that the sensing element partakes of body motion due to breathing of the wearer and a detector remote from the sensing element, the detector being responsive to motion of the sensing element for monitoring the breathing, wherein the sensing element contains no internal moving parts or circuitry, contains no battery or other source of electrical power whatsoever, requires no electrical contact with the wearer or with any other object, and requires no constraining or confining clothing, webbing, or the like. The sensing element comprises permanent magnet apparatus and the detector comprises magnetic detector apparatus for monitoring a magnetic field caused by the magnet and for monitoring variation of the magnetic field, whereby the variation of the magnetic field corresponds to the breathing.

In accordance with another aspect of the invention, the detector is coupled to a recorder.

In accordance with another aspect of the invention, the detector includes apparatus for indicating a rate of breathing outside of a predetermined rate limit and for providing an alarm signal when the motion is outside of the predetermined rate limit, the detector comprising apparatus for providing the alarm signal when a measured rate of variation of the magnetic field is detected to be outside of the predetermined rate limit, whereby the alarm signal indicates the rate of breathing to be outside of the predetermined rate limit.

In accordance with another aspect of the invention, when the rate of breathing is below a limit value such that an interruption of breathing exceeds a predetermined time interval, the detector provides the alarm signal when no variations of the magnetic field are detected within the predetermined time interval, whereby the alarm signal indicates the interruption of breathing exceeds the predetermined time interval.

In accordance with another aspect of the invention, when the rate of breathing is above a limit value, the detector provides the alarm signal when a greater rate of variation of the magnetic field is detected than the limit value, whereby the alarm signal indicates the rate of breathing exceeds the limit value.

In accordance with another aspect of the invention, apparatus for monitoring breathing and for indicating an interruption of breathing exceeding a predetermined time interval, includes a sensing element adapted to be worn by a wearer so that the sensing element partakes of body motion due to breathing of the wearer and a detector, remote from the sensing element, and being responsive to motion of the sensing element for providing an alarm signal when the motion is interrupted for longer than the predetermined time interval. The sensing element comprises permanent magnet apparatus and the detector comprises magnetic detector apparatus for monitoring a magnetic field caused by the magnet and for providing the alarm signal when no variations of the magnetic field are detected within the time interval, whereby the alarm signal indicates the interruption of breathing exceeding a predetermined time interval.

In accordance with another aspect of the invention, a breathing monitor for monitoring body movement of a wearer caused by breathing comprises a magnet for producing a magnetic field, the magnet being coupled to a wearer's body so as to move therewith when the wearer breathes, a detector for monitoring the magnetic field, and an alarm coupled to the detector.

In accordance with another aspect of the invention, the magnet is remotely positioned from the detector.

In accordance with another aspect of the invention, the magnet is affixed to the wearer's bed.

In accordance with another aspect of the invention, the magnet is affixed on the underside of the bed.

In accordance with another aspect of the invention, a breathing monitor includes a further detector, substantially similar to the first-mentioned detector, the further detector and the magnet being mutually separated by a distance that is great in comparison with the amplitude of the movement of the magnet in accordance with the wearer's breathing movements and wherein imaginary straight lines joining each of the detectors to the magnet form a non-zero angle therebetween.

In accordance with another aspect of the invention, a breathing monitor for monitoring body movement of a wearer caused by breathing, the monitor comprises a magnet for producing a magnetic field, the magnet being coupled to a wearer's body so as to move therewith when the wearer breathes, a detector for monitoring the magnetic field, and an apparatus for data recording coupled to the detector.

In accordance with another aspect of the invention, a method for monitoring breathing comprising the steps of: affixing a magnet for movement with a wearer's body movement due to breathing; monitoring a magnetic field produced by the magnet at a given distance therefrom; and evaluating variations in the magnetic field representative of the body movement due to breathing.

In accordance with another aspect of the invention, a method for monitoring breathing comprising the steps of: affixing a magnet for movement with a wearer's body movement due to breathing; monitoring a magnetic field produced by the magnet at a given distance therefrom; and recording variations in the magnetic field representative of the body movement due to breathing.

In accordance with another aspect of the invention, a method for monitoring breathing comprising the steps of: affixing a magnet for movement with a wearer's body movement due to breathing; monitoring a magnetic field produced by the magnet at a given distance therefrom; evaluating variations in the magnetic field representative of the body movement due to breathing; detecting an absence over a predetermined period of time of the variations in the magnetic field representative of the body movement due to breathing; and upon the occurrence of such absence, actuating an alarm.

In accordance with another aspect of the invention, a method for monitoring breathing comprising the steps of: affixing a magnet for movement with a wearer's body movement due to breathing; monitoring a magnetic field produced by the magnet at a given distance therefrom; evaluating variations in the magnetic field representative of the body movement due to breathing; and upon the occurrence of a rate of variations exceeding a limit rate, actuating an alarm.

In accordance with another aspect of the invention, a method for monitoring and treating breathing comprising the steps of: affixing a magnet for movement with a wearer's body movement due to breathing; monitoring a magnetic field produced by the magnet at a given distance therefrom; evaluating variations in the magnetic field representative of the body movement due to breathing; detecting an absence over a predetermined period of time of the variations in the magnetic field representative of the body movement due to breathing; and upon the occurrence of such absence, actuating a stimulation device for attempting to restore breathing.

BRIEF DESCRIPTION OF THE DRAWING

The invention will be more fully understood by way of the following detailed description, in conjunction with the drawing, in which

FIG. 8 shows a block schematic diagram of a magnetic detector system and signal processing unit in accordance with the invention;

FIG. 10 shows a block schematic diagram of a digital signal processing unit in accordance with the invention;

DETAILED DESCRIPTION OF THE PREFERRED EMBODIMENTS

Figure 1B:
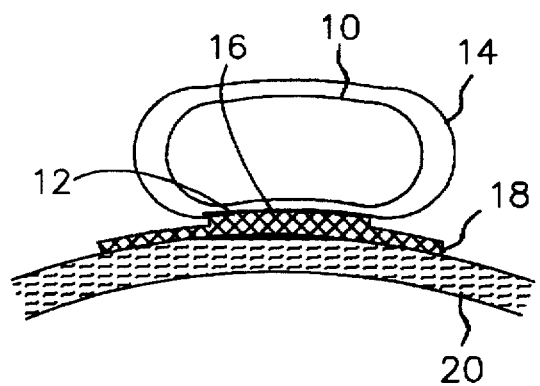
FIG. 1 shows an example of a magnet and cover in accordance with the invention, in isometric and end elevation section and not necessarily to scale.
Figure 1A:
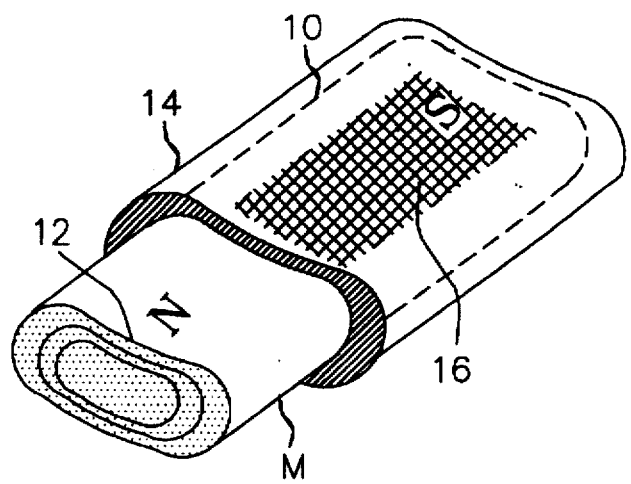

FIG. 1A shows an isometric view and FIG. 1B a cross-sectional elevation of an exemplary embodiment of a magnet 10 in accordance with the invention. 10 is a small magnet, exhibiting North-seeking and South-seeking poles, N and S, respectively. Magnet 10 is preferably of a form having a degree of concavity, as indicated at 12, so as to be adapted for more comfortable contact with a body contour. Preferably, magnet 10 is encased in a pouch 14 made of suitable fabric material. Pouch 14 exhibits a Velcro™ lining 16 arranged for cooperative engagement with a mating Velcro™ liner 18 lining a portion of an article of clothing 20 covering an infant wearer's abdomen (not shown). When pouch 14 is affixed by mating of Velcro™ liners 16 and 18, magnet 10 will move in accordance with the motion of the infant wearer's abdomen, including motion due to breathing.

Figure 2:
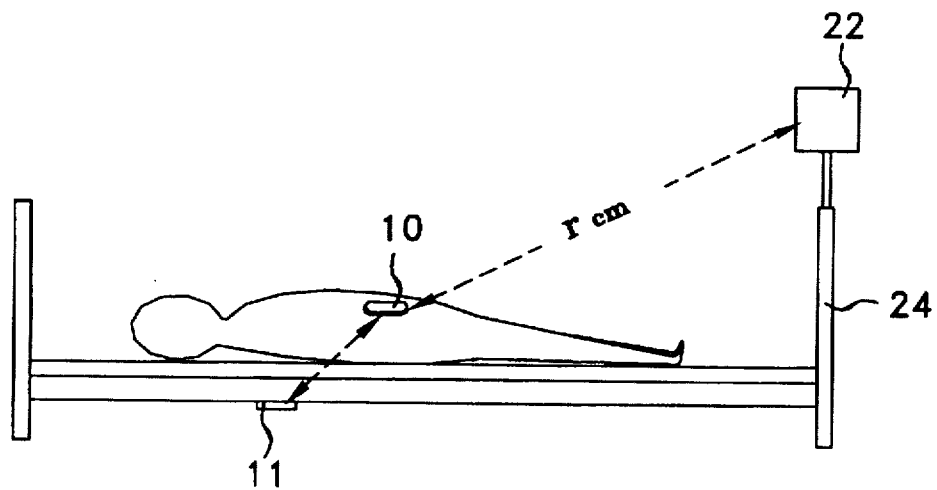
FIG. 2 shows a general configuration of an embodiment of the invention, including a magnet and a detector in accordance with the invention and not necessarily to scale.

FIG. 2 shows a detector 22 for detecting the magnetic field attributable to magnet 10, herein shown as being affixed in the region of the infant's abdomen. Detector 22 is mounted to a relatively fixed location, such as a wall or a portion of the bed or crib 24 in which the infant sleeps, or preferably affixed to the underside of the bed as shown at 11, under the mattress, or box spring, or on the floor. The distance between detector 22 and magnet 10 is designated as r centimeters (cm) and is most conveniently and preferably in the range of less than 60 cm up to 180 cm, that is between less than 2 feet up to about 6 feet, though distances smaller or greater that this range are possible. Positioning detector 22 under the bed has the advantage of making distance r very small, so that the requirement for sensitivity in detector 22 becomes very modest and a very moderately priced unit is all that is needed.

Detector 22 comprises a transducer type of sensor for magnetic fields, such as a Hall effect device, a magnetostrictive transducer, a magnetic field sensitive transistor, a search coil, a nuclear magnet resonance device, a fluxgate transducer, or other sensitive device for sensing and measuring a magnetic field intensity.

Detector 22 provides an electrical output signal indicative of the magnetic field strength present in the immediate vicinity of detector 22. As the infant breaths, its abdomen will move in and out, thereby causing distance r to vary in rhythm with the breathing. The magnetic field strength in the immediate vicinity of detector 22 will consequently vary in an inverse manner with distance r: the greater r becomes, the weaker is the field, and vice versa. The output signal of detector 22 will therefore exhibit variations due to the motion of magnet 10 in consequence of the breathing movements of the wearer's body. The signal will be in the form of a relatively steady or quasi-steady component, corresponding to the average strength of the magnetic field, having superimposed thereupon a variable component. The quasi-steady component may change as a result of displacement or rolling of the wearer's body, but in general, such changes will occur relatively infrequently and will not occur during a period of apnea. The variable component may therefore be readily separated out for further processing by using well-known techniques such as analog filtering or by analog to digital conversion and thereafter using digital filtering. So long as the variable component is present, normal breathing can be presumed to continue.

In an exemplary embodiment, the variable component is arranged to repeatedly reset a timing circuit having an operating period of about 15-20 seconds or other period determined to be desirable for identifying an occurrence of apnea. Upon a cessation of the variable component, the timing element will time out and is arranged to trigger an alarm upon such timing out.

An analysis of the magnetic field and its variations follows. This is based on the theory of magnetostatics, as may be found in any textbook on classical magnetism and electricity. See, for example, "The classical theory of electricity and magnetism," by Abraham and Becker, Blackie & Son, London, second edition, 1950; "Magnetism and electricity for students," by Hadley, MacMillan and Co., London, 1920; "Handbook of engineering fundamentals," by Eshbach, John Wiley & Sons, Inc., New York, 1952; "Standard handbook for electrical engineers," ed. Fink and Carroll, McGraw-Hill Book Company, New York, 1968; and "Physical Formulae," by Thomas, Methuen & Co., New York, 1953.

In conformity with the units used in the cited literature, the centimeter-gram-second system of electromagnetic units (c.g.s.-e.m.u. system) is used herein. Conversion to S.I. or M.K.S. units is straightforward as set forth in standard engineering handbooks.

The magnetic field strength in gauss at a distance of r cm from magnet 10, having a dipole moment of M pole-cm oriented at an angle θ exhibits a radial component given by $$R(r) = \frac{2M\cos\theta}{r^3}$$

and a tangential component given by $$T(r) = \frac{M\sin\theta}{r^3}$$

As is apparent, either R(r) or T(r) can become zero depending the orientation of magnet 10. However, the sum of the squares will not become zero for any orientation. Also, the root of the sum of the squares of R(r) and T(r) will not become zero for any orientation of magnet 10 but rather, it will undergo a 2:1 magnitude variation depending on magnet orientation.

The dipole moment of a magnet is a property of a magnet depending on the strength of its magnetization and its dimensions. Given the attractive power of a magnet or its field strength at the magnetized surface, and its dimensions, it is a straightforward calculation to obtain its dipole moment using, for example, the information found in the above-cited textbook by Hadley. Modern magnets can provide very high magnetism levels in a small size, using materials such as neodymium-iron-boron and rare earth-cobalt magnets. See for example, the catalog of Edmund Scientific Cc)., Barrington, N.J.

In the present exemplary calculations, a dipole moment of 25000 pole-cm is used. The results of using other values of dipole moment will be proportional to the ratio of dipole moment to the value used herein.

Figure 3:
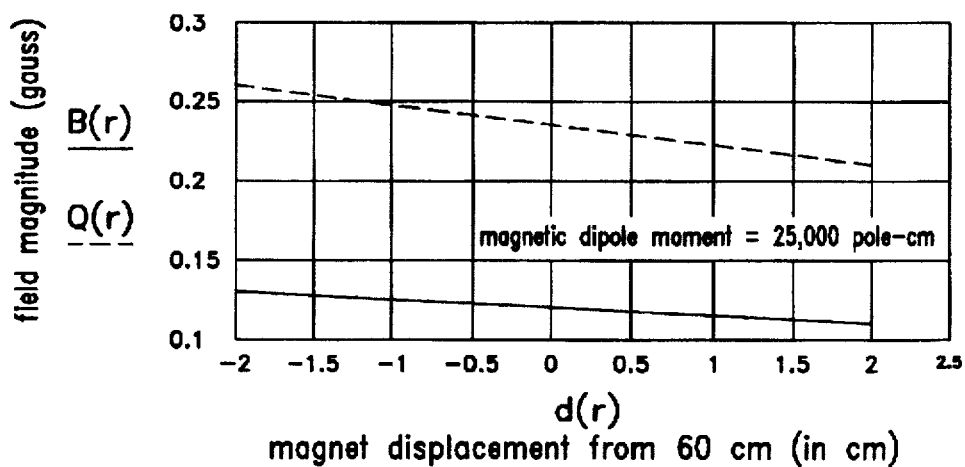
FIGS. 3–7 show calculated graphs of magnetic field quantities helpful in understanding the invention.
Figure 4:
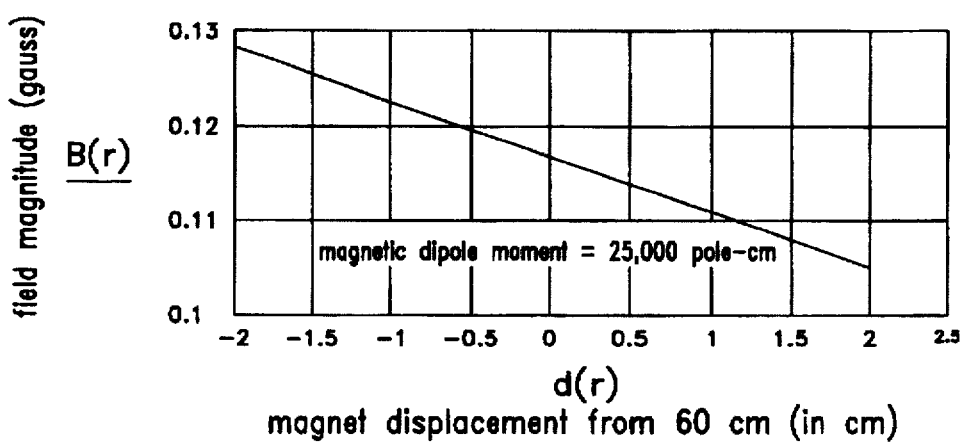
Figure 5:
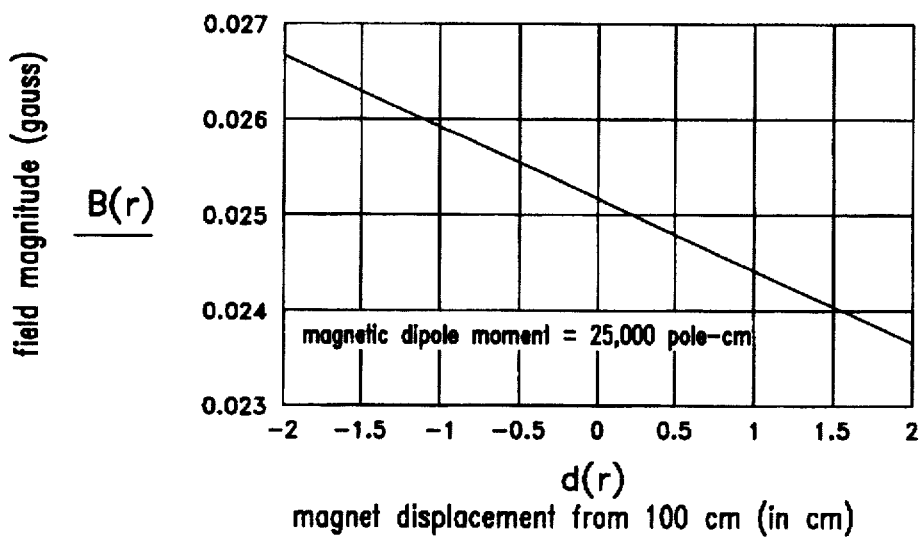
Figure 6:
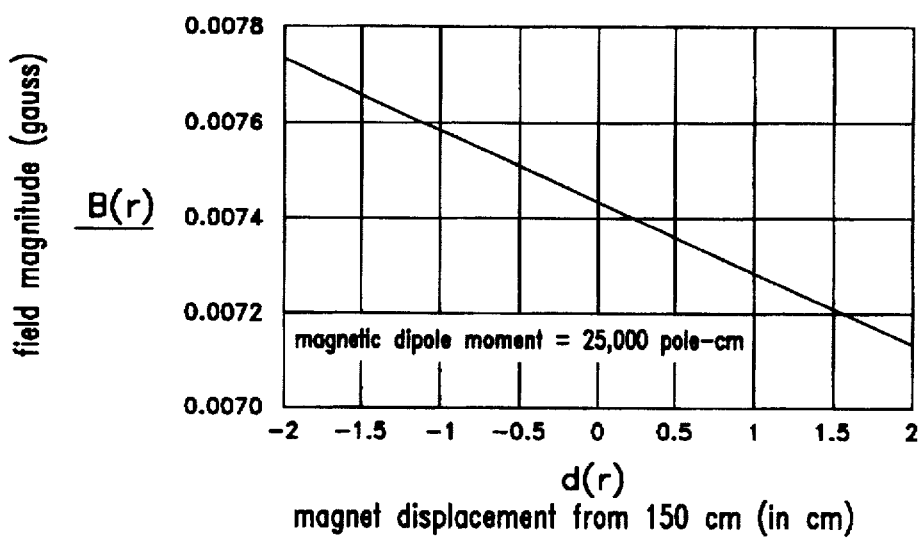
Figure 7:
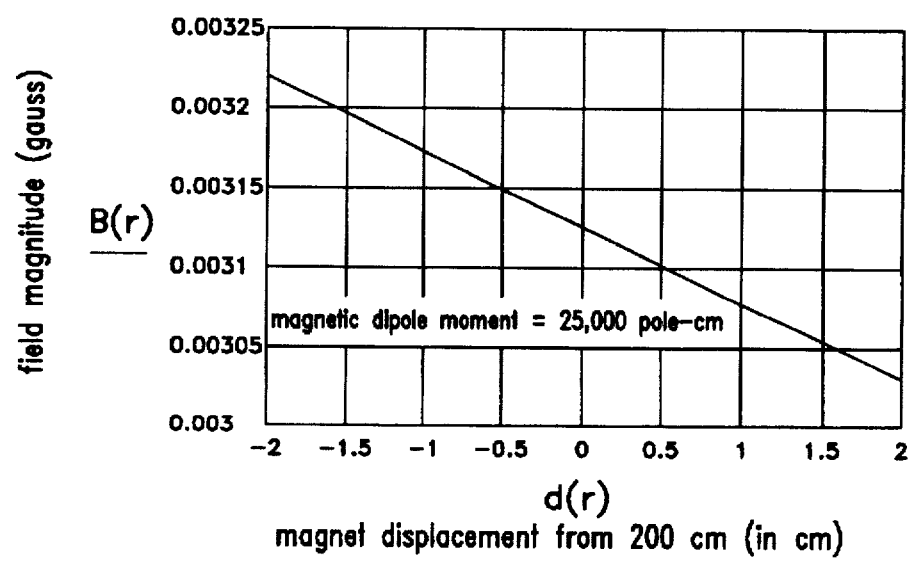

Defining $$B(r) = \sqrt{T(r)^2 + R(r)^2} \quad \text{for } \theta = 90°$$

and $$Q(r) = \sqrt{T(r)^2 + R(r)^2} \quad \text{for } \theta = 0°$$

the calculated results for r=60 cm are plotted in FIG. 3, for magnet movement of up to plus and minus 2 cm from the mean position. B(r) is shown as a solid line and Q(r) is dashed. The graph clearly shows the extreme values for the 2:1 possible variation with magnet orientation. In the subsequent graphs, the smaller value, B(r) is utilized as a "worst case" figure, with the understanding that the magnetic field will typically be somewhat stronger than the figures obtained, and may be up twice as strong, depending on the orientation of magnet 10.

FIGS. 4, 5, 6, and 7 show the variation of B(r) in gauss as a function of movements of up to plus and minus 2 cm, for mean distances r between magnet 10 and detector 22 of 60 cm, 100 cm, 150 cm, and 200 cm, respectively.

The results are summarized in Table 1, below:

TABLE 1

Field variation due to magnet movement
Magnetic dipole = 25000 pole-cm

| Distance of magnet to sensor (cm) | Magnitude of field (Gauss) | Magnet movement (cm) | Total variation in field (Gauss) | Total variation in field (percent) |
|---|---|---|---|---|
| 60 cm | 0.116 | +/−0.5 cm | 5.8 × 10⁻³ | 5% |
|  |  | +/−1.0 cm | 0.012 | 10% |
|  |  | +/−2.0 cm | 0.023 | 20% |
| 100 cm | 0.025 | +/−0.5 cm | 7.5 × 10⁻⁴ | 3% |
|  |  | +/−1.0 cm | 1.5 × 10⁻³ | 6% |
|  |  | +/−2.0 cm | 3 × 10⁻³ | 12% |
| 150 cm | 0.00741 | +/−0.5 cm | 1.5 × 10⁻⁴ | 2% |
|  |  | +/−1.0 cm | 3.0 × 10⁻⁴ | 4% |
|  |  | +/−2.0 cm | 6.0 × 10⁻⁴ | 8% |
| 200 cm | 0.00312 | +/−0.5 cm | 4.7 × 10⁻⁵ | 1.5% |
|  |  | +/−1.0 cm | 9.4 × 10⁻⁵ | 3% |
|  |  | +/−2.0 cm | 1.9 × 10⁻⁵ | 6% |

The field strength at 200 cm is 3.12 milligauss and a plus and minus movement of 1 cm due to breathing causes a change of 3%. Detection of magnetic fields in this range is readily performed and the detection of the accompanying variation is feasible using a relatively small detector apparatus. Nonetheless, it is advantageous to operate at smaller distances, if possible, such as 100 cm or 150 cm (40"–60"), since detection and evaluation of a higher field strength such as 25 milligauss is cheaper yet in terms of the apparatus required. Given the size of a typical infant or adult bed, it is perfectly feasible to mount detector 22 at the foot of the bed, for example, at a distance in the order of 100 cm or so from magnet 10 or under the bed at 20–30 cm, and thus be able to utilize a very inexpensive form of detector.

It is noted that in the event magnet 10 is moved a considerable distance away and out of range of detector 22, the result will be to indicate an alarm. The system is thus "fail-safe" in that it will not indicate normal breathing when no measurable magnetic field is available at detector 22 since the variation of zero is also zero.

FIG. 8 shows a block schematic for an exemplary embodiment of detector 22. A magnetic field detecting device oriented for sensing the radial magnetic component of the field produced by magnet 10, together with its associated circuitry, is shown at 26. The output of 26 is detected for producing an automatic gain control signal (AGC) in AGC unit 28 for controlling the output of 26 with a time constant that is very much slower than the rate of breathing or the duration of apnea before an alarm is given. Thus variations having a long period, such as due to a periodic shifting of position, can be compensated so as to keep the output signal within the permissible design dynamic range for the system. However, a system with a wide dynamic range will have no need for AGC which may then be omitted.

The output of AGC unit 28, or alternatively, unit 26 is then squared in squaring circuit 30, or processed by an absolute value circuit, as known in the art.

A parallel path is provided for the tangential magnet field component detection through unit 32, AGC unit 34, and squaring circuit 36. The respective outputs of squaring circuits 30 and 36 are summed in unit 38 whose output is then differentiated by unit 40, which may take the form of an operational amplifier differentiating circuit. The output of differentiating circuit 40 is then passed through a DC restoring type of circuit 42 wherein the negative peaks of the signal from differentiator 40 are reset to zero level so that the resulting reset signal is always positive-going and has a known datum level. The reset signal from DC restorer 42 is applied to a level detector 44 which detects crossings of a predetermined threshold level and upon the occurrence of such a crossing produces a reset pulse which is applied to a reset terminal 50 of a timer 48. Level detector 44 has a programmable threshold level by way of a programming input 46.

Optionally, the output of level detector 44 is applied to a counter 49 for keeping a record of respiration rate over a period of time such as over 24 hours, as may be needed in the diagnosis and treatment of apnea. Such a recorder may utilize magnetic or solid state storage or, for example, it may be a pen recorder and chart. Optionally, the output of level detector 44 is applied to a high rate alarm 51 for providing an alarm when the breathing rate exceeds a predetermined level such as, for example, 25 breaths per minute which, in an adult, is a serious symptom of respiratory distress. The recorder and/or high rate alarm may be connected at other points in the system, such as at the output of summing circuit 38 as shown for a counter/recorder 39; however, the output of level detector 44 is preferred because it provides one unambiguous signal for each breath comprising a contraction and an expansion.

Timer 48 has its period settable by way of programming input 52. The output of timer 48 is applied to a trigger terminal 56 of an alarm unit 54 which is provided with a reset control 58.

Figure 9A:
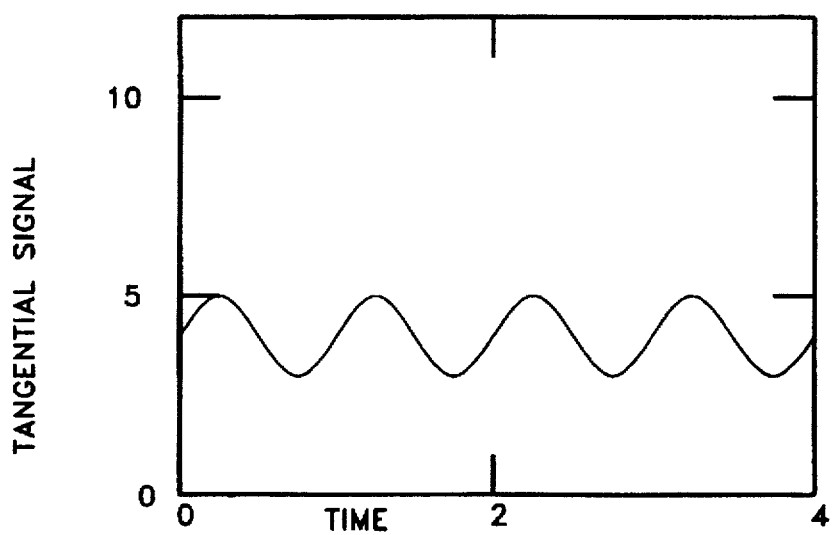
FIG. 9 shows illustrative symbolic waveforms helpful in understanding the operation of the system shown in FIGS. 8 and 10.
Figure 9B:
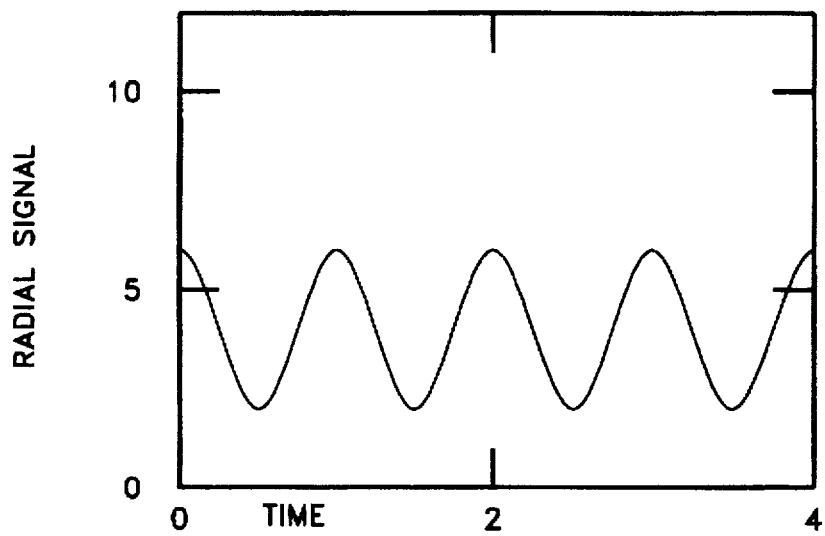
Figure 9C:
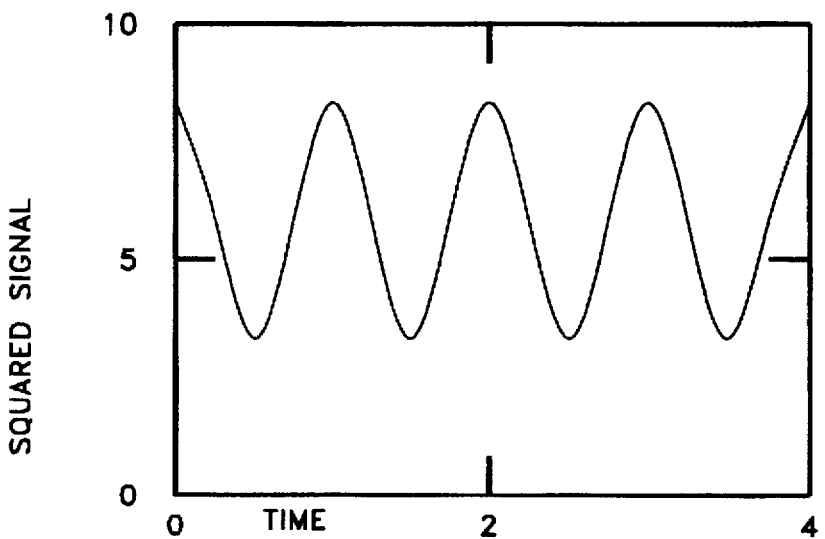
Figure 9D:
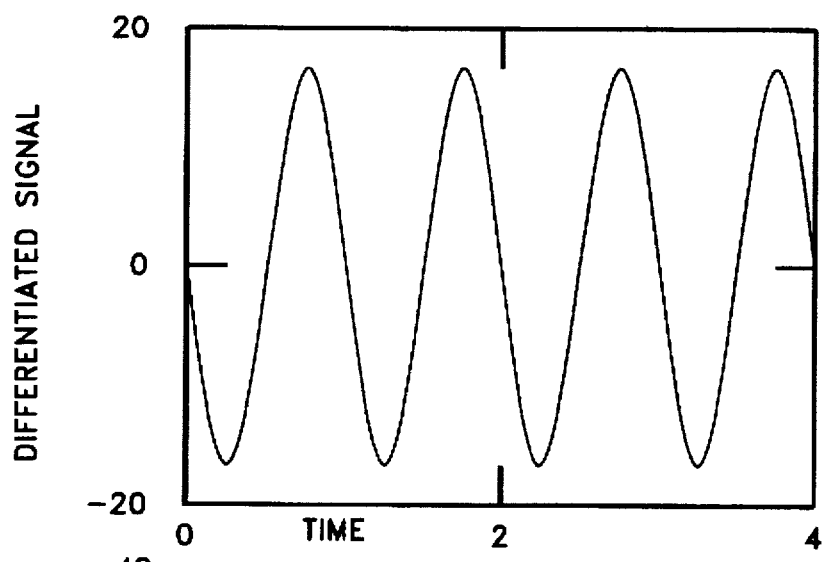
Figure 9E:
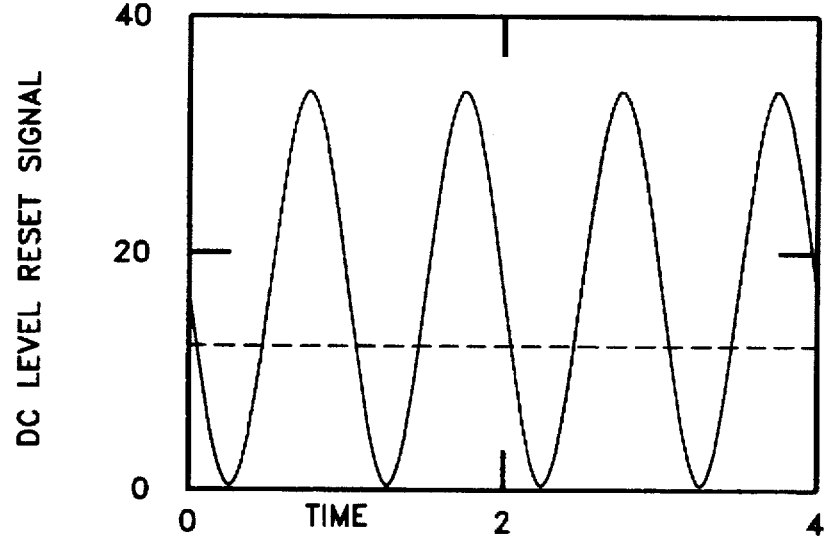
Figure 9F:
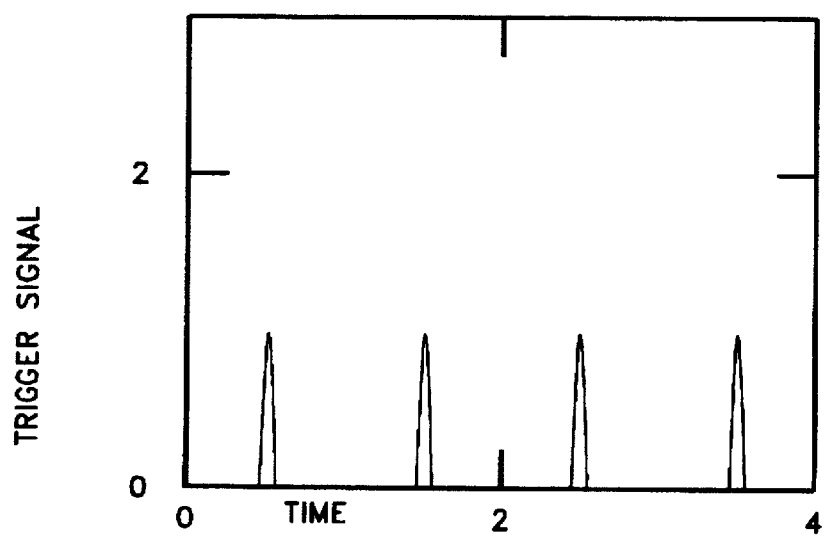

In operation, a typical output of unit 32 is indicated symbolically in FIG. 9(a). FIG. 9(b) indicates symbolically a typically output of unit 26. The signal at the output of summing circuit 38 is indicated in FIG. 9(c) and the output of differentiator 40 is indicated in FIG. 9(d). As is apparent and expected, differentiator 40 indicates plus and minus polarity slopes in its input signal, the waveform of FIG. 9(c) and it ignores the DC component whose derivative is zero. The signal after DC restorer or resetter 42, with its negative peaks clamped to ground potential is shown in FIG. 9(e). FIG. 9(e) also shows a threshold level, shown by a dashed line, of level detector 44 and FIG. 9(f) shows output pulses from level detector 44 occurring at points where the threshold voltage is crossed by a positive-going signal. Accordingly, so long as output pulses from level detector 44 are provided at intervals smaller than the period of timer 50, the timer will always be reset before alarm 54 is triggered. For a longer interval between pulses, timer 50 will time out and trigger alarm 54 to indicate an incident of apnea. It is noted that FIG. 9 waveforms are not intended to be precisely drawn to scale for actual signals or time but intended to be only indicative of the general nature of the signals involved.

Digital signal processing is also possible, as indicated in FIG. 10. Here, the output of a summing circuit 38' is converted to digital format by an analog to digital converter (A/D) 60 before being applied to a microprocessor 62 which is programmed by way of a program input 64. Microprocessor 62 performs digital threshold comparison and when the conditions are met, operates alarm 58'. It is noted that the squaring function and other functions here shown as preceding A/D converter 60; however, such functions can also be performed by microprocessor 62.

Figure 11:
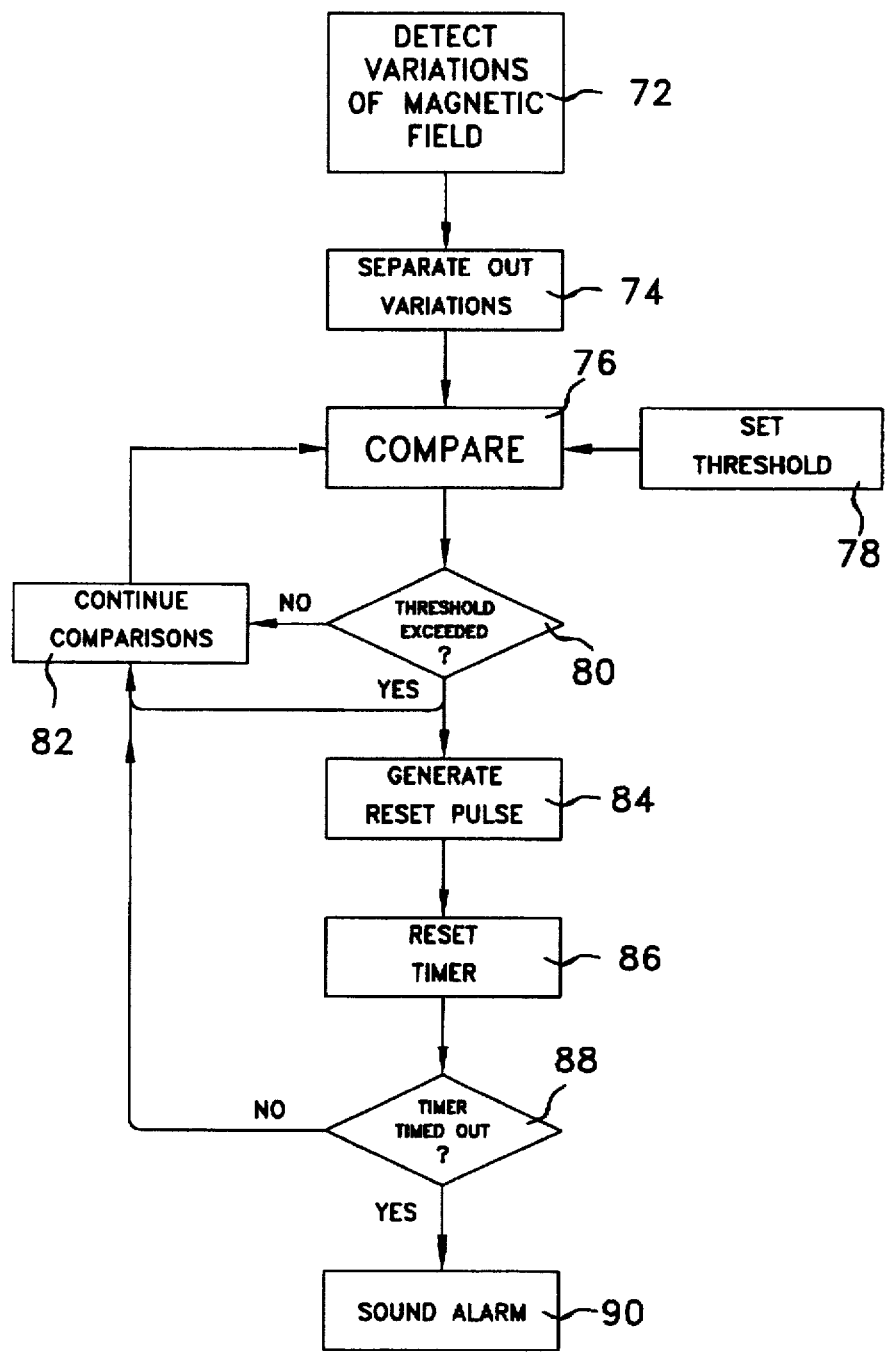
FIG. 11 shows a flow chart helpful in understanding steps of the invention.

FIG. 11 shows a flow chart beginning with the detection process of the resultant magnetic field at box 72. Variations are separated out at box 74 and a comparison made in box 76 against a threshold set in box 78. If the threshold is not exceeded, as indicated at decision box 80 comparison continues, by way of box 82. If the threshold is exceeded, comparison still continues and simultaneously, a pulse is generated at box 84 for resetting the timer at box 86. If the timer is reset before it has timed out, comparison continues by way of box 82. If no pulse has reset the timer before it has timed out, a signal is provided to activate the alarm as indicated at decision box 88 and box 90.

Figure 12:
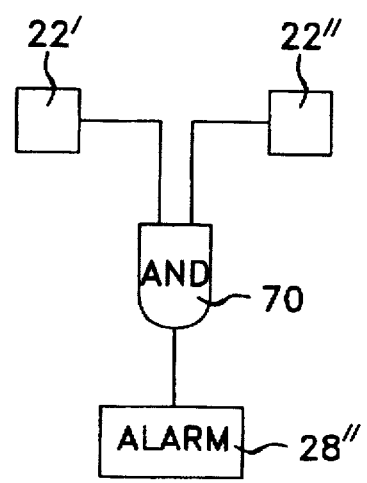
FIGS. 12 and 13 show other embodiments in accordance with the invention.
Figure 13:
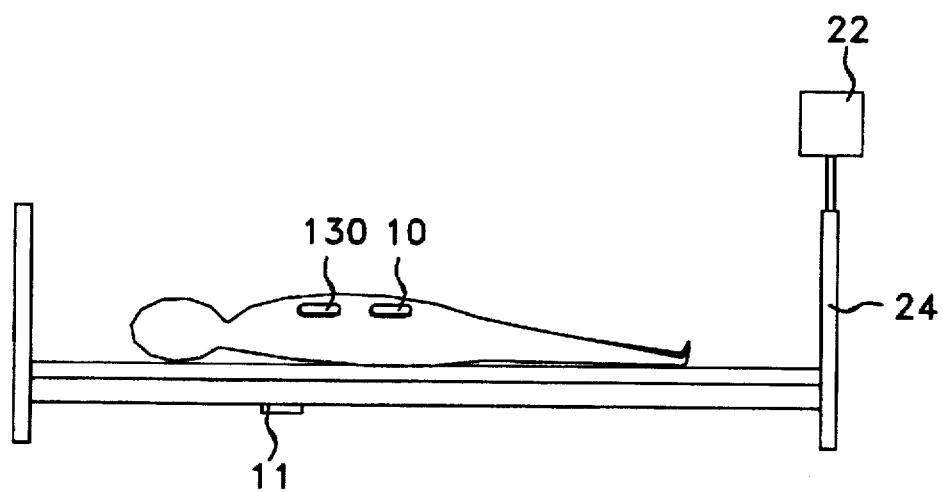

Furthermore, a plurality of detectors may by used with one magnet or with a plurality of magnets, as also one detector may used with a plurality of magnets, as for example, one magnet on the chest and another on the abdomen. See FIG. 13, showing a further magnet 130. In the case where two detectors are used, for example, one at each end of a bed so as to allow for migratory movements of the wearer over a greater range, the detector outputs can be coupled together in an AND logical configuration so that the alarm is activated only when both detectors indicate an apnea occurrence. See FIG. 12 which shows two modified detectors 22' and 22" whose outputs are coupled to the inputs of an AND gate 70. The output of AND gate 70 provides the trigger signal for alarm 28".

It is noted that the present invention meets the goal of not requiring any powered equipment to be in contact with or even close to the wearer. Only a quasi-static magnetic field is required and no electromagnetic radiation in the commonly understood meaning of the term is involved. The system is particularly immune to interference from 60 Hz or 50 Hz supply wiring and appliances since the rate of change of the magnetic field is measured at the breathing rate, that is, in terms of a few cycles per minute.

The invention has been described by way of exemplary embodiments. Various changes and modifications will be apparent to one of skill in the art to which it pertains. For example, the particular shape of magnet 10 and the means employed for attaching or affixing it, directly or indirectly to the wearer may be varied. Essentially a bar magnet can be utilized, as well as other shapes, such as a disk or a cube or, in fact, just about any convenient or compact shape. A rounded shape for magnet 10 is considered more comfortable. However, a flexible magnet may also be used if sufficient field strength for the required operating range is available. Direct adhesive application of the magnet is also envisaged. Furthermore, the detector may be a plug-in type operating on line power, or it may be battery operated, in view of the very modest power requirements of the detector and circuitry when it is in its normal monitoring mode and not operating the alarm. The alarm may be an audible warning or a flashing light, or it may be a wired, infrared, or radio link to another unit or, for example, to a telephone or local area network, such as to a hospital nurse station. In addition to an alarm, the output of detector 22 may be used to automatically initiate resuscitation measures to restore breathing, if so desired. These and like changes are intended to be within the spirit and scope of the invention, as defined by the claims following.

What is claimed is:

1. Apparatus for monitoring breathing and for indicating a rate of breathing outside of a predetermined rate limit, including a sensing element adapted to be worn by a wearer so that said sensing element partakes of body motion due to breathing of said wearer and a detector, remote from said sensing element, and being responsive to motion of said sensing element for providing an alarm signal when said motion is outside of said predetermined rate limit, wherein said sensing element contains no internal moving parts or circuitry, contains no battery or other source of electrical power whatsoever, requires no electrical contact with said wearer or with any other object, and requires no constraining or confining clothing, webbing, or the like, wherein said sensing element comprises permanent magnet means; and said detector comprises magnetic detector means for monitoring a magnetic field caused by said magnet and for providing said alarm signal when a measured rate of variation of said magnetic field is detected to be outside of said predetermined rate limit, whereby said alarm signal indicates said rate of breathing to be outside of said predetermined rate limit.

2. Apparatus for monitoring breathing, including a sensing element adapted to be worn by a wearer so that said sensing element partakes of body motion due to breathing of said wearer and a detector remote from said wearer and from said sensing element, said detector being responsive to motion of said sensing element for monitoring said breathing, wherein said sensing element contains no internal moving parts or circuitry, contains no battery or other source of electrical power whatsoever, requires no electrical contact with said wearer or with any other object, and requires no constraining or confining clothing, webbing, or the like, wherein said sensing element comprises permanent magnet means; and said detector comprises magnetic detector means for monitoring a magnetic field caused by said magnet and for monitoring variation of said magnetic field, whereby said variation of said magnetic field corresponds to said breathing.

3. Apparatus for monitoring breathing in accordance with claim 2, wherein said detector is coupled to a recorder.

4. Apparatus for monitoring breathing in accordance with claim 2, wherein said detector includes means for indicating a rate of breathing outside of a predetermined rate limit and for providing an alarm signal when said motion is outside of said predetermined rate limit, said detector comprising means for providing said alarm signal when a measured rate of variation of said magnetic field is detected to be outside of said predetermined rate limit, whereby said alarm signal indicates said rate of breathing to be outside of said predetermined rate limit.

5. Apparatus for monitoring breathing in accordance with claim 4, wherein when said rate of breathing is below a limit value such that an interruption of breathing exceeds a predetermined time interval, said detector provides said alarm signal when no variations of said magnetic field are detected within said predetermined time interval, whereby said alarm signal indicates said interruption of breathing exceeds said predetermined time interval.

6. Apparatus for monitoring breathing in accordance with claim 4, wherein when said rate of breathing is above a limit value, said detector provides said alarm signal when a greater rate of variation of said magnetic field is detected than said limit value, whereby said alarm signal indicates said rate of breathing exceeds said limit value.

7. Apparatus for monitoring breathing and for indicating an interruption of breathing exceeding a predetermined time interval, including a sensing element adapted to be worn by a wearer so that said sensing element partakes of body motion due to breathing of the wearer and a detector, remote from said sensing element, and being responsive to motion of said sensing element for providing an alarm signal when said motion is interrupted for longer than said predetermined time interval, wherein said sensing element contains no internal moving parts or circuitry, contains no battery or other source of electrical power whatsoever, utilizes no electrical contact with said wearer or with any other object, and requires no constraining or confining clothing, webbing, or the like, wherein said sensing element comprises permanent magnet means; and said detector comprises magnetic detector means for monitoring a magnetic field caused by said magnet and for providing said alarm signal when no variations of said magnetic field are detected within said time interval, whereby said alarm signal indicates said interruption of breathing exceeding a predetermined time interval.

8. A breathing monitor for monitoring body movement of a wearer caused by breathing, said monitor comprising:

a magnet for producing a magnetic field, said magnet being coupled to a wearer's body so as to move therewith when said wearer breathes;

a detector for monitoring said magnetic field; and an alarm coupled to said detector.

9. A breathing monitor in accordance with claim 8, wherein said magnet is remotely positioned from said detector.

10. A breathing monitor in accordance with claim 9, wherein said detector is affixed to said wearer's bed.

11. A breathing monitor in accordance with claim 10, wherein said detector is affixed on the underside of said bed.

12. A breathing monitor in accordance with claim 8, wherein said detector monitors variations in said magnetic field representative of said wearer breathing and, when said variations are no longer present over a predetermined period of time, said detector causes said alarm to operate.

13. A breathing monitor in accordance with claim 8, wherein said detector monitors a tangential magnetic field component and a radial magnetic field component relative to an imaginary line joining said detector to said magnet.

14. A breathing monitor in accordance with claim 13, wherein respective magnitude signals independent of polarity are derived from said longitudinal magnetic field component and said radial magnetic field component and a summation signal is derived from both magnitude signals.

15. A breathing monitor in accordance with claim 14, wherein variations in said summation signal representative of said wearer breathing are detected and, when said variations are no longer present over a predetermined period of time, said detector causes said alarm to operate.

16. A breathing monitor for monitoring movement of a user's body caused by breathing, said monitor comprising:
 a permanent magnet for producing a magnetic field in ambient space, said magnet being coupled to a wearer's body so as to move therewith in accordance with said wearer's breathing movements when said wearer breathes and thereby cause variations of said magnetic field;
 a detector for monitoring said magnetic field; and
 an alarm coupled to said detector for providing an alarm signal when said detector detects a predetermined change in said variations of magnetic field.

17. A breathing monitor in accordance with claim 16, wherein during normal breathing of said wearer, said variations of said magnetic field occur at a normal rate corresponding to a range of normal breathing rate and said predetermined change defines variations at an alarm rate, less than a given amount below said normal rate.

18. A breathing monitor in accordance with claim 17, wherein said alarm rate includes a rate of zero, that is, corresponding to a complete cessation of breathing.

19. A breathing monitor in accordance with claim 16, wherein said detector comprises a magnetometer for detecting variations in said ambient magnetic field.

20. A breathing monitor in accordance with claim 19, wherein said detector comprises a Hall effect device.

21. A breathing monitor in accordance with claim 19, wherein said detector comprises a semiconductor device responsive to magnetic fields.

22. A breathing monitor in accordance with claim 19, wherein said detector comprises a search coil device.

23. A breathing monitor in accordance with claim 16, wherein said detector includes amplifier and filter means for selecting a frequency range including said normal rate.

24. A breathing monitor in accordance with claim 16, wherein said detector includes means for deriving a change signal from said variations of said magnetic field.

25. A breathing monitor in accordance with claim 24, wherein said detector includes differentiating means for deriving said change signal from said variations of said magnetic field.

26. A breathing monitor in accordance with claim 25, wherein said detector includes means for detecting an absence of said change signal.

27. A breathing monitor in accordance with claim 26, wherein said detector includes timing means for detecting an absence of said change signal over a predetermined period of time.

28. A breathing monitor in accordance with claim 27, wherein said detector provides said alarm signal after said absence of said change signal over said predetermined period of time.

29. A breathing monitor in accordance with claim 16, wherein said detector and said permanent magnet are mutually separated by a distance that is great in comparison with the amplitude of said movement of said magnet in accordance with said wearer's breathing movements.

30. A breathing monitor in accordance with claim 16, including a further detector, substantially similar to said first-mentioned detector, said further detector and said magnet being mutually separated by a distance that is great in comparison with the amplitude of said movement of said magnet in accordance with said wearer's breathing movements and wherein imaginary straight lines joining each of said detectors to said magnet form a non-zero angle therebetween.

31. A breathing monitor in accordance with claim 16, including a further detector, substantially similar to said first-mentioned detector, said further detector and said magnet being mutually separated by a distance that is great in comparison with the amplitude of said movement of said magnet in accordance with said wearer's breathing movements and wherein imaginary straight lines joining each of said detectors to said magnet form substantially a right angle therebetween.

32. A breathing monitor for monitoring body movement of a wearer caused by breathing, said monitor comprising:
 a magnet for producing a magnetic field, said magnet being coupled to a wearer's body so as to move therewith when said wearer breathes;
 a detector for monitoring said magnetic field;
 an alarm coupled to said detector; and wherein said detector monitors variations in said magnetic field representative of said wearer breathing and, when said variations occur at a rate exceeding a predetermined rate, said detector causes said alarm to operate.

33. A breathing monitor for monitoring body movement of a wearer caused by breathing, said monitor comprising:
 a magnet for producing a magnetic field, said magnet being coupled to a wearer's body so as to move therewith when said wearer breathes;
 a detector for monitoring said magnetic field; and
 a means for data recording coupled to said detector.

34. A breathing monitor as recited in claim 33, including a plurality of magnets for producing magnetic fields, said magnets being coupled to a wearer's body so as to move therewith when said wearer breathes.

35. A breathing monitor as recited in claim 34, including an AND gate and wherein said detectors have their respective outputs coupled to inputs of said AND gate, the output of said AND gate providing a combined output signal.

36. A breathing monitor as recited in claim 33, including a plurality of detectors for monitoring said magnetic field.

37. A method for monitoring breathing comprising the steps of:
 affixing a magnet for movement with a wearer's body movement due to breathing;
 monitoring a magnetic field produced by said magnet at a given distance therefrom and from said wearer's body; and
 evaluating variations in said magnetic field representative of said body movement due to breathing.

38. A method for monitoring breathing comprising the steps of:
 affixing a magnet for movement with a wearer's body movement due to breathing;
 monitoring a magnetic field produced by said magnet at a given distance therefrom and from said wearer's body; and recording variations in said magnetic field representative of said body movement due to breathing.

39. A method for monitoring breathing comprising the steps of:

affixing a magnet for movement with a wearer's body movement due to breathing;

monitoring a magnetic field produced by said magnet at a given distance therefrom;

evaluating variations in said magnetic field representative of said body movement due to breathing;

detecting an absence over a predetermined period of time of said variations in said magnetic field representative of said body movement due to breathing; and upon the occurrence of such absence, actuating an alarm.

40. A method for monitoring breathing comprising the steps of:

affixing a magnet for movement with a wearer's body movement due to breathing;

monitoring a magnetic field produced by said magnet at a given distance therefrom;

evaluating variations in said magnetic field representative of said body movement due to breathing; and upon the occurrence of a rate of variations exceeding a limit rate, actuating an alarm.

41. A method for monitoring breathing and treating apnea, comprising the steps of:

affixing a magnet for movement with a wearer's body movement due to breathing;

monitoring a magnetic field produced by said magnet at a given distance therefrom;

evaluating variations in said magnetic field representative of said body movement due to breathing;

detecting an absence over a predetermined period of time of said variations in said magnetic field representative of said body movement due to breathing; and upon the occurrence of such absence, actuating a stimulation device for attempting to restore breathing.

* * * * *